(12) United States Patent
Querleux et al.

(10) Patent No.: US 7,901,355 B2
(45) Date of Patent: Mar. 8, 2011

(54) SKIN ANALYSIS APPARATUS INCLUDING AN ULTRASOUND PROBE

(75) Inventors: Bernard Querleux, Le Perreux (FR); Thérèse Baldeweck, Vincennes (FR); Mathias Fink, Meudon (FR); Jean-Luc Genisson, Paris (FR)

(73) Assignee: L'Oreal, Paris (FR)

( * ) Notice: Subject to any disclaimer, the term of this patent is extended or adjusted under 35 U.S.C. 154(b) by 1479 days.

(21) Appl. No.: 10/759,215

(22) Filed: Jan. 20, 2004

(65) Prior Publication Data

US 2004/0225215 A1    Nov. 11, 2004

Related U.S. Application Data

(60) Provisional application No. 60/464,853, filed on Apr. 24, 2003.

(30) Foreign Application Priority Data

Jan. 23, 2003  (FR) ................................. 03 00721

(51) Int. Cl.
*A61B 5/00* (2006.01)
(52) U.S. Cl. .................................. 600/438
(58) Field of Classification Search ................ 600/442, 600/443, 438, 447
See application file for complete search history.

(56) References Cited

U.S. PATENT DOCUMENTS

| | | | | |
|---|---|---|---|---|
| 4,206,769 A | * | 6/1980 | Dikstein | 600/587 |
| 4,610,255 A | | 9/1986 | Shimura et al. | |
| 5,099,848 A | | 3/1992 | Parker et al. | |
| 5,115,808 A | * | 5/1992 | Popovic et al. | 600/438 |
| 5,139,020 A | * | 8/1992 | Koestner et al. | 607/24 |
| 5,415,173 A | * | 5/1995 | Miwa et al. | 600/447 |
| 5,524,636 A | * | 6/1996 | Sarvazyan et al. | 600/587 |
| 5,545,124 A | * | 8/1996 | Krause et al. | 601/2 |
| 5,555,891 A | * | 9/1996 | Eisenfeld | 600/534 |
| 5,606,791 A | | 3/1997 | Fougere et al. | |
| 5,706,815 A | * | 1/1998 | Sarvazyan et al. | 600/438 |
| 5,810,731 A | | 9/1998 | Sarvezyan et al. | |
| 5,895,356 A | * | 4/1999 | Andrus et al. | 600/439 |
| 6,273,864 B1 | | 8/2001 | Duarte et al. | |
| 6,425,873 B1 | * | 7/2002 | Marchitto et al. | 600/573 |

(Continued)

FOREIGN PATENT DOCUMENTS

AU    762374    10/2000

(Continued)

OTHER PUBLICATIONS

Volume 12 Issue 4 p. 279-282, Nov. 2006, Skin Research and Technology, Gérald E. Piérard, MD, PhD.*

(Continued)

*Primary Examiner* — Brian Casler
*Assistant Examiner* — Jonathan G Cwern
(74) *Attorney, Agent, or Firm* — Banner & Witcoff, Ltd.

(57) ABSTRACT

The present invention relates to an analysis apparatus for analyzing the skin, the which includes an ultrasound probe arranged to analyze the skin along an axis and a vibrator arranged to emit at least one shear wave to a region of the skin extending about the axis. The ultrasound probe is arranged to detect displacements induced in the skin by the propagation of the shear wave.

34 Claims, 2 Drawing Sheets

U.S. PATENT DOCUMENTS

| | | | |
|---|---|---|---|
| 6,488,639 B1* | 12/2002 | Ribault et al. | 601/2 |
| 6,656,116 B2* | 12/2003 | Kim et al. | 600/300 |
| 6,770,033 B1* | 8/2004 | Fink et al. | 600/443 |
| 2001/0007940 A1* | 7/2001 | Tu et al. | 606/41 |
| 2002/0007118 A1* | 1/2002 | Adachi et al. | 600/443 |
| 2002/0010398 A1* | 1/2002 | Bonnefous | 600/442 |
| 2002/0095087 A1* | 7/2002 | Mourad et al. | 600/442 |
| 2002/0151767 A1* | 10/2002 | Sonnenschein et al. | 600/117 |
| 2004/0064050 A1* | 4/2004 | Liu et al. | 600/457 |
| 2005/0251042 A1 | 11/2005 | Sandrin et al. | |

FOREIGN PATENT DOCUMENTS

| | | |
|---|---|---|
| FR | 2 655 835 | 6/1991 |
| FR | 2 811 524 | 1/2002 |
| JP | 64-83248 | 3/1989 |
| JP | 10-328184 | 12/1998 |
| JP | 11137525 | 5/1999 |
| WO | WO 01/80742 | 11/2001 |

OTHER PUBLICATIONS

Vogt, M., et al. "In vivo evaluation and imaging of skin elasticity applying high frequency (22MHz) ultrasound", Ultrasonics Symposium, 2002. Proceedings. 2002 IEEE, pp. 1863-1866.

Translation of Official Action in Japanese application 2004-16028, Jan. 24, 2007.

Japanese Second Office Action for JP2004-16028 dated Mar. 26, 2008.

* cited by examiner

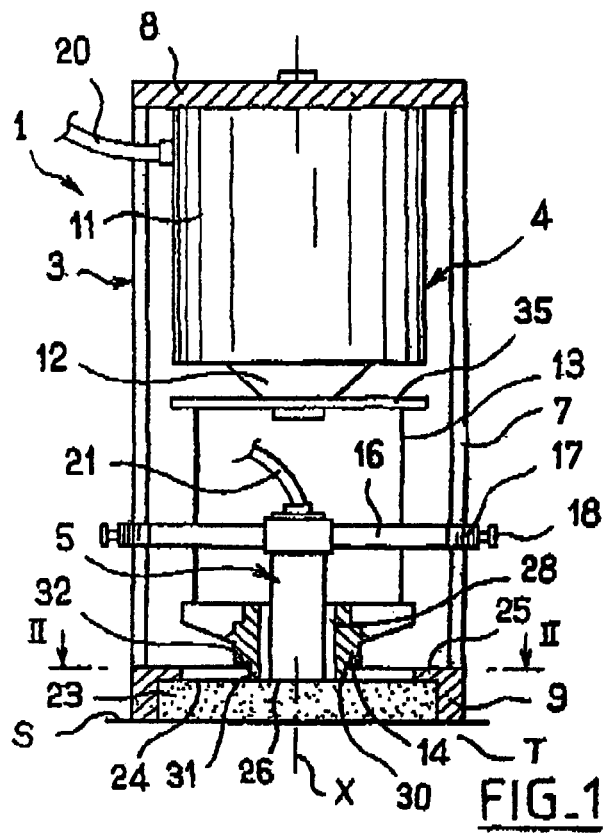
FIG_1
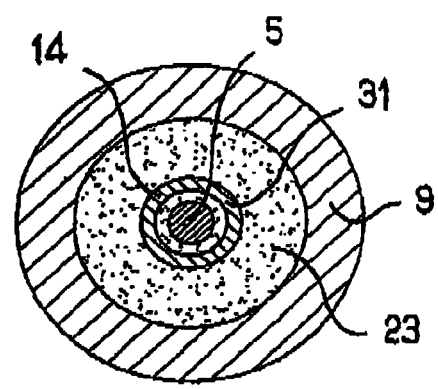
FIG_2
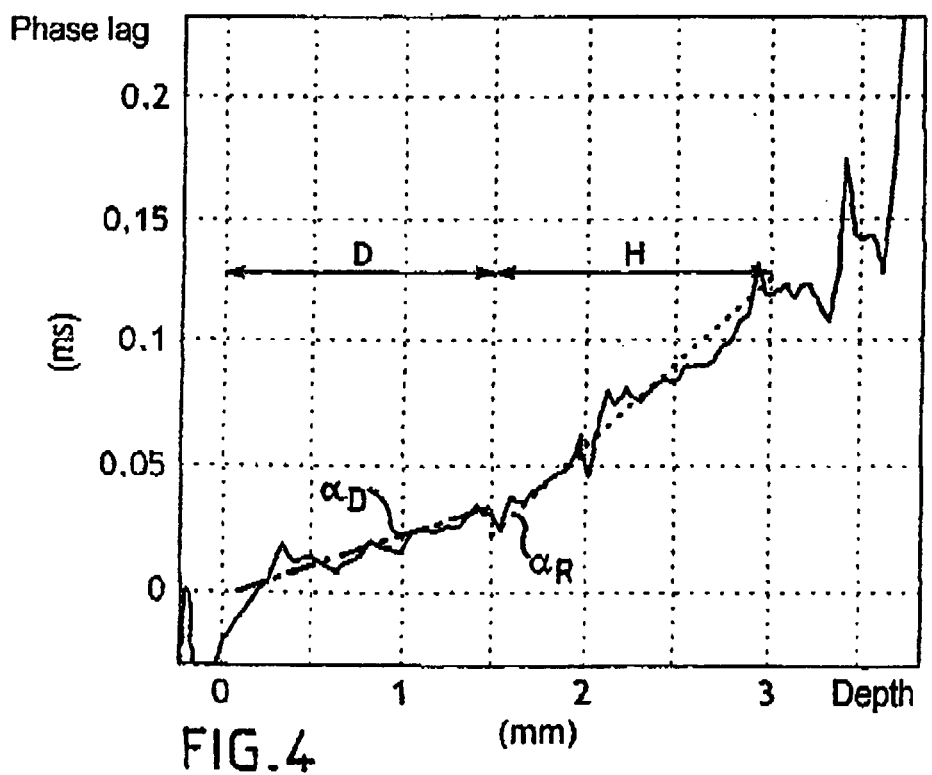
FIG_4

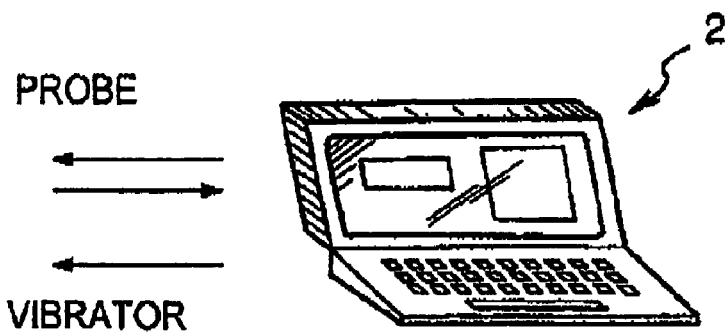
FIG_3
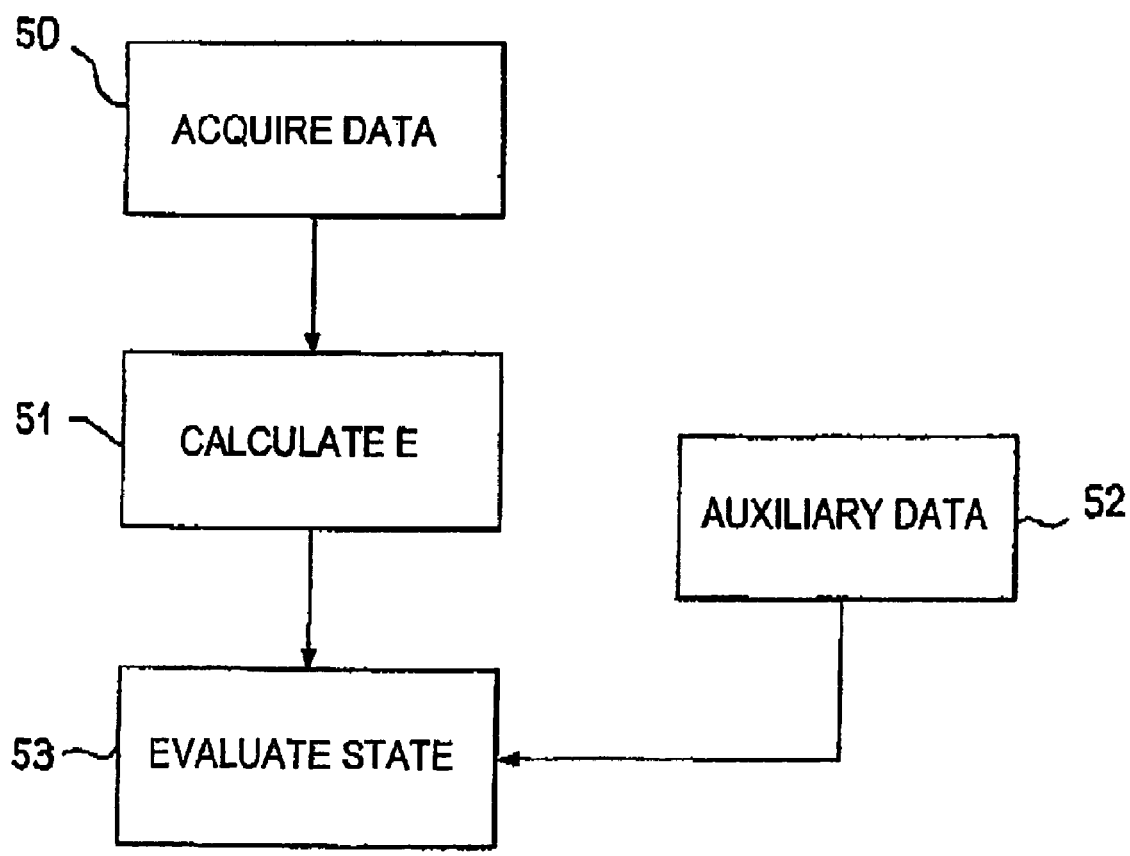
FIG_5

SKIN ANALYSIS APPARATUS INCLUDING AN ULTRASOUND PROBE

This application claims the benefit of French application No. 03 00721 filed Jan. 23, 2003 and of U.S. Provisional Application No. 60/464,853 filed on Apr. 24, 2003, the disclosures of which are incorporated by reference herein.

FIELD OF THE INVENTION

The present invention relates to methods and apparatus for analyzing the human skin.

The invention relates more particularly, but not exclusively, to apparatus in which useful information relating to at least one property of tissue is obtained by using an ultrasound probe to analyze the propagation of a shear wave in said tissue. Such apparatus is described in international application WO 00/55616.

The present invention seeks to propose apparatus that enables the skin to be analyzed over a shallow depth from its surface, in order, for example, to determine the Young's modulus and the shear modulus of the various constituent layers of the dermis and of the hypodermis, and to determine their thicknesses, where appropriate.

SUMMARY OF THE INVENTION

In one of its aspects amongst others, the invention provides a skin analysis apparatus which comprises:
  an ultrasound probe arranged to analyze the skin along an axis; and
  a vibrator arranged to emit at least one shear wave to a region of the skin extending about the axis, the ultrasound probe being arranged to detect displacements induced in the skin by the propagation of the shear wave.

As a result of the shear wave being generated in the skin from a region extending about the axis X, it is possible to increase the amplitude of the displacements of the skin along axis X, and thus increase the accuracy of the measurement. The apparatus may include only a single ultrasound probe, and despite using only a single probe, the resulting accuracy can turn out to be satisfactory.

The apparatus may include a coupling member enabling ultrasound waves to be transmitted between the probe and the skin. Given that the probe has a focal length, the thickness of the coupling member is preferably selected so as to enable the ultrasound waves to be focused in a given region of maximum depth below the surface of the skin. The depth may be less than or equal to 4 millimeters (mm), for example, so as make it possible to analyze the mechanical properties of the dermis and of the hypodermis of the skin.

By way of example, the focal length of the ultrasound probe may lie in the range 10.4 mm to 15.6 mm, being equal to about 13 mm, for example, in a particular embodiment of the invention.

By way of example, the thickness of the coupling member may lie in the range 10.6 mm to 14.4 mm, being equal to about 12 mm, for example, when the above-mentioned focal length is about 13 mm.

The coupling member may comprise a layer of viscoelastic material presenting a Young's modulus that is close to the Young's modulus of the skin, e.g. a Young's modulus lying in the range 0.25 mega pascals (MPa) to 25 MPa, e.g. 0.5 MPa to 25 MPa, in particular about 0.5 MPa. By way of example, the layer of viscoelastic material may be a layer of gel, in particular a gel including gelatine at a concentration lying in the range 5% to 25%, in particular about 10%.

By way of example, the viscoelastic material of the coupling member may be in the form of a disk, in particular a disk of substantially constant thickness, the disk being suitable for holding against the surface of the skin by a holding ring provided with an inwardly-directed rim against which the face of the disk remote from the skin can bear. The ring can form part of a frame to which the vibrator and the probe are secured, the frame preferably being made so as to enable the apparatus to be positioned on the surface of the skin in such a manner that the axis X is substantially perpendicular to the surface of the skin.

The vibrator may include an annular piece defining a contact surface from which the shear wave is emitted to the skin, the annular piece presenting a central bore in which the ultrasound probe extends.

The contact surface may present symmetry about the axis X, and in particular circular symmetry about the axis X. The shear wave can thus be emitted into the skin by excitation that is omnidirectional about the axis X.

The probe may be arranged to emit and receive ultrasound waves at a frequency lying in the range 1 megahertz (MHz) to 300 MHz for example, preferably in the range 10 MHz to 300 MHz, more preferably in the range 30 MHz to 70 MHZ, and most preferably greater than 40 MHz, e.g. about 50 MHz. Such a frequency makes it possible to obtain satisfactory axial resolution, e.g. better than 100 micrometers ($\mu$m). The vibrator may include an electro-magnetic device comprising a coil, for example, and the analysis apparatus may include a generator arranged to deliver a low-frequency signal to the vibrator during the entire analysis period, e.g. a signal having a frequency lying in the range 100 hertz (Hz) to 500 Hz, and of about 300 Hz in a particular embodiment of the invention. Such a signal is quickly attenuated in the human skin, and can avoid generating too much disturbance resulting from echoes. The vibrator may also include at least one pneumatic or hydraulic member, in which case the shear wave is generated from a variation in the pressure of a gas or of a liquid.

The analysis apparatus may include a processor device arranged to deliver at least one piece of information, representative of a mechanical property of at least one layer of the skin, from signals picked up by the ultrasound probe. The information may include the value of the Young's modulus and/or of the shear modulus and/or of the thickness of the dermis or of the hypodermis.

The processor device may be arranged to deliver information relating to the state of the skin, e.g. its degree of aging, by comparing the measured value with reference values.

The processor device may be arranged to store the signals picked up by the ultrasound probe at various successive time points, e.g. at n time intervals dt, dt lying in the range 0.2 milliseconds (ms) to 0.8 ms for example, and n lying in the range 50 to 500, and so as to perform statistical processing of the picked-up signals so as to improve the signal to noise ratio.

By way of example, the statistical processing may include calculating a mean value for its Young's modulus E, or for its shear modulus $\mu$, or for the propagation speed Vs of the shear wave.

The probe and the vibrator are advantageously arranged so that the displacement of the vibrator along the axis X for generating the shear wave is not transmitted to the probe.

In an exemplary embodiment, the vibrator emits the shear wave to the skin through the coupling member. The coupling member can thus advantageously contribute to ensuring that the shear wave which reaches the analysis region in a form suitable for measurement, i.e. in particular, being far enough away from the place where it originated.

The apparatus may be arranged in such a manner that at least one of the ultrasound probe and of the vibrator is connected to a processor device such as a microcomputer, but it is not beyond the ambit of the present invention for the probe, the vibrator, and the processor device to be integrated within a portable appliance, e.g. a hand-held appliance, said appliance including an application face for application to the skin, and at least one display, for example, making it possible to deliver information relating to the analyzed region.

The vibrator may also include at least one nozzle enabling a jet of liquid or of compressed gas, e.g. compressed air, to be directed onto the surface of the skin or of a coupling member.

The vibrator may also include means enabling the shear wave to be generated by exerting low pressure locally on the skin or on the coupling member.

Where appropriate, the apparatus, and in particular the measurement acquisition part designed to be in contact with the skin, may include one or more sensors for measuring hydration, the microrelief of the skin, pH, temperature or color, or the humidity at the surface of the tissue, for example, and it may even include a biosensor. In an exemplary embodiment, the skin analysis apparatus comprises:

an ultrasound probe for analyzing the skin along an axis x;

a vibrator arranged to emit at least one shear wave to a region of the skin extending along the axis, the ultrasound probe being capable of detecting displacements induced in the skin by the propagation of the shear wave; and a coupling member, said coupling member being selected to enable the ultrasound waves emitted by the ultrasound probe to be focused in a given region of maximum depth below the surface of the skin, said depth being less than or equal to 4 mm, for example.

In another of its aspects, the invention also provides a skin analysis method which comprises analyzing the skin by means of apparatus as described above.

In an exemplary implementation of the invention, the method may further comprise processing signals coming from the ultrasound probe so as to determine at least one value relating to mechanical properties of the skin, in particular its Young's modulus, its shear modulus $\mu$, or the propagation speed Vs of the shear wave.

The method may also comprise processing the signals coming from the ultrasound probe to determine the thickness of the dermis or of the hypodermis.

Processing the signals may comprise calculating the phase lag of the shear wave as a function of the depth.

Processing the signals may comprise a method of processing by crosscorrelation, as described in the above-mentioned international application WO 00/55616, whose content is incorporated herein by reference.

Processing may seek to determine a state of the skin, in particular a degree of aging of said skin, e.g. by comparing a value for Young's modulus as determined by analyzing the skin with reference values, thus making use of the fact that both Young's modulus and the propagation speed of the shear wave in the dermis tend to be smaller in young people than in old people.

Processing may also seek to determine the tension of the skin, given that both the propagation speed of the shear wave, and Young's modulus are greater in a tense medium than in a slack medium.

In another of its aspects, the invention also provides a skin evaluation method comprising:

analyzing the skin by means of apparatus as defined above; and delivering, from the results of the analysis, information relating to at least one mechanical property of said region, e.g. its elasticity.

Where appropriate, information can be supplied relating to the anisotropy of the collagen fibers in the plane of the skin, in particular if the shear wave is emitted into the skin via a vibrator contact surface presenting a shape that is not omnidirectional, e.g. the contact surface being defined by a bar instead of by an annular piece.

The results of two evaluations of the skin, in particular two values of Young's modulus, at two different time points can be compared, and information relating to the variation of at least one mechanical property of the skin, in particular its elasticity, between said two time points can be delivered. This makes it possible, for example, to inform the individual under evaluation about the effect of treatment.

It is also possible to evaluate the mechanical properties, in particular the elasticity, of a region of the body that is not exposed to a given environment, for example that is not exposed to the sun, and to evaluate a region of the body that is exposed to said environment, and compare results, so that by comparing said results information can be determined that is of use in evaluating the aging of the skin, for example.

It is also possible to analyze tissue with the sensor in a first geographical location, for example in a beauty parlor, at a point-of-sale, or at home, and to transmit the data obtained by the apparatus remotely over a network such as the Internet, an Intranet, or a mobile telephone network, and then process said data in a second geographical location, e.g. a research center, for the purpose of evaluating a property of the skin, e.g. its elasticity.

The result of the evaluation may be transmitted over a network such as the Internet, an Intranet, or a mobile telephone network. It is also possible to transmit the result of the evaluation by post. The result of the evaluation may be accompanied, where appropriate, with a prescription for a product that has action on the state of the skin, e.g. its elasticity.

The apparatus may include a measurement acquisition part designed to be applied on various regions of the body and in particular on the arm, the forearm, or the thigh.

If necessary, measurements may be performed while the arm is tensed and then relaxed, so as to determine the influence of tension of the skin on the measured values of Young's modulus, for example In an implementation of the invention, information is stored relating to the analysis performed, e.g. relating to the elasticity of the skin, and the values are compared in order to reveal, for example, an improvement or a deterioration over time in the state of the skin, and in particular its elasticity.

In another of its aspects, the invention also provides a method of prescribing a product, in particular a cosmetic, which method may comprise:

evaluating a mechanical characteristic, e.g. the elasticity of the skin, by implementing the method as defined above; and in the light of the result of the evaluation, prescribing a cosmetic having an effect on said characteristic.

The term "cosmetic product" is used to designate a product as defined in EC Council Directive 93/35 dated Jun. 14, 1993.

In another of its aspects, the invention also provides a method of determining the effectiveness of treatment that has action on a mechanical property of the skin, in particular on the elasticity or on the tension of the skin, the method comprising:

performing a first evaluation of said mechanical property;
performing the treatment; and after the treatment, performing a second evaluation of said mechanical property, at least one of the first and second evaluations being performed by implementing a method as defined above. Preferably, both evaluations are performed by implementing the same method.

In another of its aspects, the invention also provides a method of treating a region of the body, the method comprising:

evaluating a mechanical property of the skin, in particular the elasticity or the tension of the skin in said region, by implementing a method as defined above; and performing treatment that has action on said mechanical property in the light of the result of the evaluation. The treatment may be performed by a topical, oral, or other technique. The treatment may include complying with a particular diet or training regime or administering specific kinds of care, such as massaging.

In another of its aspects, the invention provides a method of promoting the sale of a product, in particular a cosmetic, the method including demonstrating activity or effectiveness of the product as revealed by the method above.

Such product promotion may be performed using any communications channel.

In particular, it may be performed by a sales person, directly at a point-of-sale, by radio, television, or telephone, in particular in the form of advertising spots or short messages. It may also be performed by means of the written press or by any other document, in particular for advertising purposes. It may also be performed over the Internet, or over any other suitable computer network or over a mobile telephone network. It may also be performed directly on the product, in particular on its packaging or on instructions associated therewith.

The invention applies to analyzing natural human skin, it being possible to make the measurement in vivo, or to analyzing artificial skin.

BRIEF DESCRIPTION OF THE DRAWINGS

The invention will be better understood on reading the following detailed description of non-limiting embodiments thereof, and on examining the accompanying drawings, in which:

FIG. 1 is a diagrammatic elevation view partially in axial section of apparatus constituting an embodiment of the invention;

FIG. 2 is a cross-section on II-II of FIG. 1;

FIG. 3 is a view of a processor device in isolation for association with the measurement acquisition part of FIG. 1;

FIG. 4 is a graph showing phase lag as a function of the depth; and

FIG. 5 is a flow chart showing an example of a method of the invention.

MORE DETAILED DESCRIPTION

FIG. 1 shows the measurement acquisition part 1 of analysis apparatus for analyzing the human skin T, the apparatus being designed to measure the propagation speed of a shear wave in said skin.

The measurement acquisition part 1 is connected to a processor device 2 which is shown diagrammatically in FIG. 3 and which is constituted, for example, by a conventional microcomputer provided with appropriate cards providing the interface with the measurement acquisition part 1.

The measurement acquisition part comprises a frame 3 supporting a vibrator 4 and a ultrasound probe 5, said part having an axis X.

More particularly, in the embodiment under consideration, the frame 3 comprises a plurality of parallel rods 7 fixed at their top ends to a spacer 8 and at their bottom ends to a holding ring 9 for holding a coupling member 23. In the embodiment described, there are three rods 7.

The vibrator includes an electromagnetic mechanism comprising a coil 11 arranged to vibrate a core 12 connected, by means of a plate 35 and parallel rods 13, to an annular piece 14 whose role is explained below. By way of example, there are three rods 13.

The probe 5 is secured to arms 16 which present ends 17 which are fixed in adjustable manner on the rods 7, at a desired height, by means of screws 18. In the embodiment described, there are three arms 16.

The coil 11 and the probe 5 are connected to the processor device 2 by respective cables 20 and 21.

In the embodiment under consideration, the above-mentioned coupling member 23 is in the form of a disk of substantially constant thickness, made of a gel of gelatine at a concentration of 10%, the disk having a bottom face for resting against the surface S of the tissue T, and a top face 24 bearing against a rim 25 of the ring 9.

The surfaces of the tissue T may extend perpendicularly to the axis x of the probe.

A bottom face 26 of the probe 5 comes to bear against the top face 24 of the coupling member 23, after passing through the annular piece 14 via a central bore 28.

The annular piece 14 defines a relatively narrow contact surface 30 with the coupling member 23. In the embodiment under consideration, said contact surface 30 extends perpendicularly to the axis X, being formed by the bottom end edge of a cylindrical skirt 31 forming a step 32 relative to the remainder of the piece 14.

In the embodiment under consideration, the probe 5 comprises a transducer arranged to operate at a frequency of 50 MHz.

The processor device 2 is arranged to control the operation of the probe 5 and of the vibrator 4 in such a manner that the vibrator 4 emits a shear wave into the tissue via the coupling member 23. The shear wave propagates through the skin at a speed which depends on the Young's modulus of said skin. The probe 5 measures the displacements, along the axis X, of the various layers of the skin under the effect of said shear wave propagating.

As a function of the measured displacement amplitudes, it is possible to determine the phase lag of the shear wave at a given depth, and to calculate Young's modulus of the dermis and of the hypodermis, for example.

In the embodiment under consideration, the shear wave is generated by exciting the vibrator 4 with a sinusoidal signal at a frequency of 300 Hz, the advantage of such a frequency being that the shear wave is quickly attenuated in the skin, thereby minimizing disturbance induced by echoes of the shear wave on deeper layers of the skin.

By way of example, such a measurement acquisition cycle comprises continuously emitting a shear wave at a frequency of 300 Hz, and acquiring ultrasound images on the axis X at time intervals of 0.5 ms for example, by means of the probe 5.

In the embodiment under consideration, said probe presents a focal length of 13 mm, and the thickness of the coupling member 23 is 12 mm, such that the ultrasound waves emitted by the probe 5 are focused essentially in the first millimeters of the skin T below its surface S.

By way of example, each image along the axis X is recorded in digital form with a sampling speed of 500 MHz, the image comprising 4096 points along the axis X, for example.

The images are then processed so as to show the displacements of the various layers of tissue as a result of the shear wave propagating, it being possible to perform said processing by crosscorrelation, for example, in a manner similar to that described in the above-mentioned international application WO 00/55616.

FIG. 4 is a graph showing phase lag as a function of the depth.

In the graph, two regions D and H can be seen corresponding to the shear wave propagating in the dermis and in the hypodermis respectively.

The gradients $\alpha_D$ and $\alpha_R$ of the linear regression lines in the regions D and H enable Young's modulus E to be determined approximately in said layers.

The propagation speed Vs of the shear waves corresponds to the gradients $\alpha_D$ and $\alpha_R$ and is related to the coefficient of shear $\mu$ by the relationship:

$$V_S = \sqrt{\frac{\mu}{\rho}}$$

where $\rho$ designates the density of the medium.

In addition, in biological tissue, it is possible to approximate Young's modulus E by the following relationship:

$E \approx 3\mu$.

By way of example, the apparatus described above can be used as follows.

As shown in FIG. 5, in a first step 50, data is acquired by means of the measurement acquisition part 1, e.g. by applying the ring 9 and the coupling member 23 on the thigh, the forearm, or the arm, then at step 51, Young's modulus E is calculated for the dermis and for the hypodermis.

By comparing with auxiliary data 52, such as reference values for Young's modulus, for example, for a subject of the same sex and age as the subject being evaluated, it is possible, at step 53, to evaluate the state of the skin of said subject, in particular to show whether the skin of said subject is more or less elastic than the average, and, where necessary, to prescribe treatment for said subject for improving the suppleness of the skin or for slowing down the effects of aging.

Naturally, the invention is not limited to the embodiments described above.

It is possible, in particular, to apply various modifications to the apparatus described above, in particular to the measurement acquisition part designed to be applied on the skin. In particular, the coupling member 26 can, for example, be made in another shape, and in particular of a material other than gelatine, thereby making it possible, where necessary, to make cut-outs or recesses in the coupling member, said cut-outs or recesses being designed to improve mechanical decoupling between the ultrasound probe and the vibrator, and/or to improve the waveform of the waves emitted to the skin.

It is possible to make the piece of the vibrator designed to emit the shear wave into the skin in a shape that is not circularly symmetrical, in particular if it is desired to reveal any anisotropy of the collagen fibers.

Throughout the description, including in the claims, the term "comprising a" should be understood as being synonymous with "comprising at least one", unless specified to the contrary.

Although the present invention herein has been described with reference to particular embodiments, it is to be understood that these embodiments are merely illustrative of the principles and applications of the present invention. It is therefore to be understood that numerous modifications may be to the illustrative embodiments and that other arrangements may be devised without departing from the spirit and scope of the present invention as defined by the appended claims.

What is claimed is:

1. Analysis apparatus for analyzing skin, the apparatus comprising:
   a coupling member configured to contact a region of skin;
   an ultrasound probe having a probe surface, wherein the ultrasound probe is configured to receive data associated with the region of skin along an axis; and
   a vibrator communicatively coupled with an annular piece, the annular piece defining a contact surface and a central bore, the vibrator configured to emit at least one shear wave to the region of skin via the contact surface in contact with the coupling member,
   wherein the ultrasound probe is configured to detect a displacement induced in the region of skin by propagation of the shear wave, and
   wherein the ultrasound probe extends through the central bore along an X axis such that the probe surface contacts the coupling member and such that at least a portion of X axis displacements of the vibrator are not transmitted to the ultrasound probe.

2. Apparatus according to claim 1, wherein a thickness of the coupling member is configured to enable the focusing of ultrasound waves in a predefined region of maximum depth below a surface of the region of skin.

3. Apparatus according to claim 2, wherein the depth of said predefined region is less than or equal to 4 mm.

4. Apparatus according to claim 1, wherein a focal length of the ultrasound probe lies in the range 10.4 mm to 15.6 mm.

5. Apparatus according to claim 1, wherein a thickness of the coupling member lies in the range 10.6 mm to 14.4 mm.

6. Apparatus according to claim 1, wherein the coupling member comprises a disk of viscoelastic material.

7. Apparatus according to claim 6, wherein the coupling member is configured to be held against a surface of the skin by a holding ring provided with an inwardly-directed rim against which a face of the coupling member remote from the skin can bear.

8. Apparatus according to claim 7, including a frame to which the vibrator and the ultrasound probe are secured, wherein the frame enables the apparatus to be positioned so that the X axis is substantially perpendicular to a surface of the region of skin.

9. Apparatus according to claim 1, wherein the contact surface presents symmetry about the X axis.

10. Apparatus according to claim 1, wherein the contact surface presents circular symmetry about the X axis.

11. Apparatus according to claim 1, wherein the ultrasound probe is arranged to emit and receive ultrasound waves at a frequency lying in the range of 1 MHz to 300 MHz.

12. Apparatus according to claim 1, wherein the ultrasound probe is arranged to emit and receive ultrasound waves at a frequency lying in the range of 30 MHz to 70 MHZ.

13. Apparatus according to claim 1, wherein the ultrasound probe is arranged to emit and receive ultrasound waves at a frequency of 50 MHz.

14. Apparatus according to claim 1, including a generator arranged to deliver a low-frequency signal to the vibrator during an analysis period, the signal having a frequency lying in the range of 100 Hz to 500 Hz.

15. Apparatus according to claim 1, including a generator arranged to deliver a low-frequency signal to the vibrator during an analysis period, the signal having a frequency of about 300 Hz.

16. Apparatus according to claim 1, including a processor device configured to receive information from the ultrasound probe, wherein the information represents a mechanical property and/or a thickness of at least one layer of the skin.

17. Apparatus according to claim 16, wherein the processor device is configured to deliver state information relating to a state of the skin, by comparing a measured value with a reference value.

18. Apparatus according to claim 17, wherein the state information is indicative of an age associated with the skin.

19. Apparatus according to claim 16, wherein the processor device is configured to store the information received from the ultrasound probe at various successive time points.

20. Apparatus according to claim 16, wherein the processor device is configured to store the information received from the ultrasound probe—for each sample during a predefined time interval, the number of samples lying in the range of 50 to 500.

21. Apparatus according to claim 20, wherein the predefined time interval lies in the range of 2.2 ms to 0.8 ms.

22. The apparatus of claim 1, wherein
the ultrasound probe is configured to receive data associated with the region of skin along the X axis, and
the probe does not contact the inner walls of the central bore, such that a portion of the X axis displacements of the vibrator are not transmitted to the ultrasound probe.

23. A skin analysis method, comprising:
applying an apparatus to a region of skin associated with a patient, the apparatus comprising:
a coupling member configured to contact a region of skin;
an ultrasound probe having a probe surface, wherein the ultrasound probe is configured to receive data associated with the region of skin along an axis; and
a vibrator including an annular piece defining a contact surface and a central bore, the vibrator configured to emit at least one shear wave to the region of skin via the contact surface in contact with the coupling member
wherein the ultrasound probe is configured to detect a displacement induced in the region of skin by propagation of the shear wave, and
wherein the ultrasound probe extends through the central bore along an X axis such that the probe surface contacts the coupling member and such that at least a portion of X axis displacements of the vibrator are not transmitted to the ultrasound probe;
receiving data associated with the region of skin; and
storing the data.

24. A method according to claim 23, further comprising processing the data coming from the ultrasound probe so as to determine at least one value relating to a mechanical property of the region of skin.

25. A method according to claim 24, wherein said mechanical property is selected from the group consisting of its Young's modulus, its shear modulus, and the propagation speed of the shear wave.

26. A method according to claim 24, wherein the phase lag of the shear wave is calculated as a function of the depth.

27. A method according to claim 24, wherein a state of the region of skin is determined by comparing a value for Young's modulus resulting from analyzing the region of skin with reference values.

28. A method according to claim 27, wherein the determined state of the region of skin is indicative of a degree of aging of the skin.

29. The method of claim 23, wherein
the ultrasound probe is configured to receive data associated with the region of skin along the X axis, and
the probe does not contact the inner walls of the central bore, such that a portion of the X axis displacements of the vibrator are not transmitted to the ultrasound probe.

30. A method of evaluating a mechanical property of a region of the skin, the method comprising:
analyzing said region with the apparatus according to claim 1; and
delivering, from the results of the analysis, information relating to said mechanical property.

31. A method of determining an effectiveness of treatment that affects a mechanical property of skin, the method comprising:
performing a first evaluation of said mechanical property;
performing the treatment on the skin; and
after the treatment, performing a second evaluation of said mechanical property, at least one of the first and second evaluations including the steps of
analyzing the skin using the apparatus according to claim 1, and
processing signals coming from the ultrasound probe so as to determine at least one value relating to the mechanical property of the skin.

32. The method of claim 31, further including demonstrating activity or effectiveness of a product based on the second evaluation.

33. A method of treating a region of a human body, the method comprising:
analyzing skin using the apparatus according to claim 1;
processing signals coming from the ultrasound probe so as to determine at least one value relating to a mechanical property of the skin; and
performing treatment that affects said property based on an evaluation of the at least one value.

34. Analysis apparatus for analyzing skin, the apparatus comprising:
a coupling member configured to contact a region of skin;
an ultrasound probe having a probe surface in contact with the coupling member, wherein the ultrasound probe is configured to receive data associated with the region of skin along an axis; and
a vibrator configured to emit at least one shear wave to the region of skin via a contact surface of the analysis apparatus, the contact surface being distinct from the probe surface, and in contact with the coupling member,
wherein the ultrasound probe is configured to detect a displacement induced in the region of skin by propagation of the shear wave,
wherein the contact surface and the probe surface are substantially co-planar and the ultrasound probe extends along an X axis, and wherein at least a portion of X axis displacements of the vibrator are not transmitted to the ultrasound probe.

* * * * *